US008859237B2

United States Patent
Liang et al.

(10) Patent No.: US 8,859,237 B2
(45) Date of Patent: Oct. 14, 2014

(54) DIGUANYLATE CYCLASE METHOD OF PRODUCING THE SAME AND ITS USE IN THE MANUFACTURE OF CYCLIC-DI-GMP AND ANALOGUES THEREOF

(75) Inventors: Zhao-Xun Liang, Singapore (SG); Feng Rao, Singapore (SG)

(73) Assignee: Nanyang Technological University, Singapore (SG)

(*) Notice: Subject to any disclaimer, the term of this patent is extended or adjusted under 35 U.S.C. 154(b) by 83 days.

(21) Appl. No.: 13/203,998

(22) PCT Filed: Feb. 18, 2010

(86) PCT No.: PCT/SG2010/000060
§ 371 (c)(1),
(2), (4) Date: Aug. 31, 2011

(87) PCT Pub. No.: WO2010/101526
PCT Pub. Date: Sep. 10, 2010

(65) Prior Publication Data
US 2012/0040403 A1 Feb. 16, 2012

Related U.S. Application Data

(60) Provisional application No. 61/156,826, filed on Mar. 2, 2009.

(51) Int. Cl.
*C12P 19/36* (2006.01)

(52) U.S. Cl.
USPC .......................................................... 435/90

(58) Field of Classification Search
None
See application file for complete search history.

(56) References Cited

FOREIGN PATENT DOCUMENTS

WO     2006045041 A2     4/2006

OTHER PUBLICATIONS

Nelson et al., Nature 399: 323-329 (1999).*
Christen et al., J. Biol. Chem. 281(42): 32015-32024 (2006).*
Karaolis et al., Antimicrob. Agents and Chemotherapy 49(3): 1029-1038 (2005).*
Zamost et al., J. Industrial Microbiol. 8: 71-82 (1991).*
Shin et al., Biotechnol. Bioprocess Eng. 12: 640-645 (2007).*
Johnson et al., Mol. Microbiol. 55(3): 664-674 (2005).*
Rao et al., Enzymatic Synthesis of c-di-GMP using a thermophilic diguanylate cyclase, Analytical Biochemistry 2009, vol. 389, pp. 138-142.
Beyhan et al., Identification and Characterization of Cyclic Diguanylate Signaling Systems Controlling Rugosity in Vibrio Cholerae, Journal of Bacteriology 2008 vol. 190 pp. 7392-7405.
Romling et al., C-di-GMP: the dawning of a novel bacterial signaling system, (2005) Mol. Microbiol. 57, 629-639.
Jenal et al., Mechanisms of Cyclic-di-GMP Signaling in Bacteria, (2006) Annu. Rev. Genet 40, 385-407.
Weinhouse, H. et al., c-di-GMP-binding protein, a new factor regulating cellulose synthesis in Acetobacter xylinum, (1997) FEBS Lett 416, 207-211.
Sim et al., GGDEF and EAL domains inversely regulate cyclic di-GMP levels and transition from sessility to motility, (2004) Mol. Microbiol. 53, 1123-1134.

(Continued)

*Primary Examiner* — Patricia A Leith
*Assistant Examiner* — Erin M Bowers
(74) *Attorney, Agent, or Firm* — MKG, LLC

(57) ABSTRACT

Described is a new stand-alone diguanylate cyclase polypeptide having a GGDEF motif and a mutated I-site that does not bind c-di-GMP. We demonstrate that the production yield of c-di-GMP and analogues was significantly increased by mutation of a conserved residue in the putative regulatory I-site.

8 Claims, 7 Drawing Sheets

(56) References Cited

OTHER PUBLICATIONS

Chan et al., Structural basis of activity and allosteric control of diguanylate cyclase (2004) Proc. Natl. Acad. Sci. USA 101, 17084-17089.

Schmidt, et al., The Ubiquitous Protein Domain EAL is a Cyclic Diguanylate-Specific Phosphodiesterase: Enzymatically Active and Inactive EAL Domains, (2005) J. Bacteriol 187, 4774-4781.

Rao et al., Catalytic Mechanism of Cyclic Di-GMP-Specific Phosphodiesterase: a Study of the EAL Domain-Containing Roc-R from *Pseudomonas aeruginosa*, (2008) J. Bacteriol 190, 3622-3631.

Kararaolis et al., c-di-GMP(3-5-Cyclic Diguanylic Acid) Inhibits *Staphylococcus aureus* Cell-Cell Interactions and Biofilm Formatio, (2005) Antimicrob. agents Chemother. 49, 1029-1038.

Brouillette, et al., 3-5-Cyclic Diguanylic Acid Reduces the Virulence of Biofilm-Forming *Staphylococcus aureus* Strains in a Mouse Model of Mastitis Infection, (2005) Antimicrob. Agents Chemother. 49 pp. 3109-3113.

Karaolisa et al., 3',5'-Cyclic diguanylic acid(c-di-GMP) inhibits basal and growth factor-stimulated human colon cancer cell proliferation, (2005) Biochem. Biophys. Res. Commun 329, 40-45.

Karaolis et al., Cyclic Di-GMP timulates Protective Innate Immunity in Bacterial Pneumonia, (2007) Infect. Immun. 75, 4942-4950.

Hayakawa et al., A facile synthesis of cyclic bis(3'-5') diguanylic acid, (2003) Tetrahedron 59, 6465-6471.

Ross et al., The Cyclic Diguanylic Acid Regulatory SYstem of Cellulose Synthesis in Acetobacter xylinum, (1990) J. Biol. Chem. 265, 18933-18943.

Zhang, et al., c-di-GMP Displays a monovalent metal Ion-Dependent Polymorphism, (2004) J. Am. Chem. Soc. 126, 16700-16701.

Yan et al., Synthesis of 3', 5'-cyclic diguanylic acid (cdiGMP) using 1-(4-chlorophenyl)-4-ethoxypiperidin-4-yl as a protecting group for 2'-hydroxy functions of Ribonucleosides, (2007) Nucleosides, Nucleotides and Nucleic Acids 26, 189-204.

Kiburu et al., A simple solid-phase synthesis of the ubiquitous bacterial signaling molecule, c-di-GMP and analogues, (2008) Mol. Biosys. vol. 4, pp. 518-520.

Tamayo et al., The EAL Domain Protein VieA is a Cyclic Diguanylate Phosphodiesterase (2005) J. Biol. Chem. vol. 280, pp. 33324-3330.

Merighi et al., The second messenger bis-(3'-5')-cyclic-GMP ad tis PilZ domain-containing receptor Alg44 are required for alginate biosynthese in Psudomonas aeruginosa, (2007) Mol. Microbiol. vol. 65 pp. 876-895.

Hickman et al., Identification of FleQ from *Pseudomonas aeruginosa* as a c-di-GMP-responsive transcription factor, (2008) Mol. Microbiol. 9999.

Kazmierczak et al., Analysis of FimX, a phosphodiesterase that governs twitching motility in *Pseudomonas aeruginosa*, (2006) Mol. Microbiol. vol. 60 pp. 1026-1043.

Paul et al., Activation of the Diguanylate Cyclase PleD by Phosphorylation-mediated Dimerization, (2007) J. Biol. Chem. vol. 282 pp. 29170-29177.

Wassmann, P. et al., Structure of BeF3-Modified Response Regulator PleD: Implications for Diguanylate Cyclase Activation, Catalysis, and Feedback Inhibition (2007) Structure vol. 15 pp. 915-927.

De, et al., Phosphorylation—Independent Regulation of the Diguanylate Cyclase WspR (2008) PLoS Biology vol. 6, e67.

Ramona Neunuebel, M. et al., Journal of Bacteriology, 2008, vol. 190, pp. 6829-6836.

Rao et al., YybT Is a Signaling Protein That Contains a Cyclic Dinucleotide Phosphodiesterase DOmain and a GGDEF Domain with ATPase Activity, Jan. 1, 2010, Journal of Biological Chemistry, vol. 285, No. 1, pp. 473-482 and Additions and Corrections p. 29441.

Supplementary European Search Report dated Jun. 20, 2012; issued in conjunction with European Patent Application No. 10749022.9.

Ryjenkov et al., Cyclic Diguanylate is a Ubiquitous Signaling Molecule in Bacteria: Insights into Biochemistry of the GGDEF Protein Domain, (2005) vol. 187, pp. 1792-1798.

* cited by examiner (A)  (B)

SEQUENCE LISTING

<160> NUMBER OF SEQ ID NOS: 4

<210> SEQ ID NO 1
<211> LENGTH: 516
<212> TYPE: DNA
<213> ORGANISM: Thermotoga maritima

<400> SEQUENCE: 1

```
catatgaaag aactggaata tatggcgtat catgatccgc tgaccggcct gccgaaccgc    60
cgctatttct tcgaactggg caaccgctat ctggatctgg cgaaacgtga aggcaaaaaa   120
gttttttgtgc tgtttgttga tctggccggc tttaaagcga ttaatgatac ctatggtcat   180
ctgagcggcg atgaagtgct gaaaaccgtg agcaaacgta tcctggatcg tgtggctcgt   240
agcgatgtgt ggcgcgcta tggtggcgat gaatttacca ttctgctgta tgatatgaaa   300
gaagaatatc tgaaaagcct gctggaacgt attctgagca cctttcgtga accggtgcgt   360
gtggaaaaca acatctgag cgttaccccg aatattggtg tggcgcgttt tccggaagat   420
ggtgaaaatc tggaagaact gctgaaagtg gcggatatgc gtatgtataa agccaaagaa   480
atgaaagttc cgtattttag cctgagctaa ctcgag                            516
```

<210> SEQ ID NO 2
<211> LENGTH: 188
<212> TYPE: PRT
<213> ORGANISM: Thermotoga maritima
<220> FEATURE:
<221> NAME/KEY: DOMAIN
<222> LOCATION: (24)..(181)
<223> OTHER INFORMATION: example of GGDEF domain
<220> FEATURE:
<221> NAME/KEY: MISC_FEATURE
<222> LOCATION: (98)..(98)
<223> OTHER INFORMATION: mutation of Arginine to non-polar amino acid in
    this case Alanine
<220> FEATURE:
<221> NAME/KEY: SITE
<222> LOCATION: (107)..(111)
<223> OTHER INFORMATION: GGDEF motif

<400> SEQUENCE: 2

```
Met Gly Ser Ser His His His His His His Ser Ser Gly Leu Val Pro
1               5                   10                  15

Arg Gly Ser His Met Lys Glu Leu Glu Tyr Met Ala Tyr His Asp Pro
            20                  25                  30

Leu Thr Gly Leu Pro Asn Arg Arg Tyr Phe Phe Glu Leu Gly Asn Arg
        35                  40                  45

Tyr Leu Asp Leu Ala Lys Arg Glu Gly Lys Lys Val Phe Val Leu Phe
    50                  55                  60

Val Asp Leu Ala Gly Phe Lys Ala Ile Asn Asp Thr Tyr Gly His Leu
65                  70                  75                  80

Ser Gly Asp Glu Val Leu Lys Thr Val Ser Lys Arg Ile Leu Asp Arg
                85                  90                  95

Val Ala Arg Ser Asp Val Val Ala Arg Tyr Gly Gly Asp Glu Phe Thr
            100                 105                 110

Ile Leu Leu Tyr Asp Met Lys Glu Glu Tyr Leu Lys Ser Leu Leu Glu
        115                 120                 125

Arg Ile Leu Ser Thr Phe Arg Glu Pro Val Arg Val Glu Asn Lys His
    130                 135                 140

Leu Ser Val Thr Pro Asn Ile Gly Val Ala Arg Phe Pro Glu Asp Gly
145                 150                 155                 160

Glu Asn Leu Glu Glu Leu Leu Lys Val Ala Asp Met Arg Met Tyr Lys
                165                 170                 175

Ala Lys Glu Met Lys Val Pro Tyr Phe Ser Leu Ser
            180                 185
```

```
<210> SEQ ID NO 3
<211> LENGTH: 160
<212> TYPE: PRT
<213> ORGANISM: Acetobacter xylinum
<220> FEATURE:
<221> NAME/KEY: DOMAIN
<222> LOCATION: (1)..(160)
<223> OTHER INFORMATION: example of GGDEF domain
<220> FEATURE:
<221> NAME/KEY: MISC_FEATURE
<222> LOCATION: (77)..(77)
<223> OTHER INFORMATION: mutation of Aspartic acid to non-polar amino
      acid in this case Alanine
<220> FEATURE:
<221> NAME/KEY: SITE
<222> LOCATION: (83)..(87)
<223> OTHER INFORMATION: GGDEF motif

<400> SEQUENCE: 3

Leu Ala Glu Thr Asp Thr Leu Thr Gly Leu Leu Asn Arg Gly Gly Phe
1               5                   10                  15

Asn Thr Ala Leu Ala Asp Glu Ile Ala Arg Cys Arg Glu Pro Gly Met
            20                  25                  30

Thr Ala His Pro Ala Leu Ala Met Phe Asp Leu Asp Gly Phe Lys Gln
        35                  40                  45

Ile Asn Asp Val His Gly His His Ala Gly Asp Ile Val Leu Arg Ala
    50                  55                  60

Ile Ala Ser Arg Leu Ile Glu Leu Thr His Pro Asp Ala Pro Val Ser
65                  70                  75                  80

Arg Leu Gly Gly Asp Glu Phe Ala Val Ile Leu His Arg Thr Leu Glu
                85                  90                  95

Asp Val Ser Leu Glu Arg Tyr Met Asp Arg Leu Gln Ala Ile Leu Glu
            100                 105                 110

Arg Pro Ile Asp Ile Glu Thr Val Thr Val Ser Val Ala Gly Ser Ile
        115                 120                 125

Gly Ala Val Leu Leu Asp Gly Thr Asp Thr Met Glu Asp Val Gln Lys
    130                 135                 140

Asn Ala Asp Met Ala Met Tyr Ala Ala Lys Arg Ala Gly Gly Lys Gln
145                 150                 155                 160

<210> SEQ ID NO 4
<211> LENGTH: 188
<212> TYPE: PRT
<213> ORGANISM: Thermotoga maritima
<220> FEATURE:
<221> NAME/KEY: DOMAIN
<222> LOCATION: (24)..(181)
<223> OTHER INFORMATION: example of GGDEF domain
<220> FEATURE:
<221> NAME/KEY: MISC_FEATURE
<222> LOCATION: (98)..(98)
<223> OTHER INFORMATION: mutation of Arginine to uncharged polar amino
      acid in this case Glutamine
<220> FEATURE:
<221> NAME/KEY: SITE
<222> LOCATION: (107)..(111)
<223> OTHER INFORMATION: GGDEF motif

<400> SEQUENCE: 4

Met Gly Ser Ser His His His His His His Ser Ser Gly Leu Val Pro
1               5                   10                  15

Arg Gly Ser His Met Lys Glu Leu Glu Tyr Met Ala Tyr His Asp Pro
            20                  25                  30

Leu Thr Gly Leu Pro Asn Arg Arg Tyr Phe Phe Glu Leu Gly Asn Arg
        35                  40                  45
```

```
Tyr Leu Asp Leu Ala Lys Arg Glu Gly Lys Lys Val Phe Val Leu Phe
        50              55              60

Val Asp Leu Ala Gly Phe Lys Ala Ile Asn Asp Thr Tyr Gly His Leu
65                  70              75                      80

Ser Gly Asp Glu Val Leu Lys Thr Val Ser Lys Arg Ile Leu Asp Arg
                85              90                  95

Val Gln Arg Ser Asp Val Val Ala Arg Tyr Gly Gly Asp Glu Phe Thr
            100             105             110

Ile Leu Leu Tyr Asp Met Lys Glu Glu Tyr Leu Lys Ser Leu Leu Glu
        115             120             125

Arg Ile Leu Ser Thr Phe Arg Glu Pro Val Arg Val Glu Asn Lys His
    130             135             140

Leu Ser Val Thr Pro Asn Ile Gly Val Ala Arg Phe Pro Glu Asp Gly
145                 150             155                     160

Glu Asn Leu Glu Glu Leu Leu Lys Val Ala Asp Met Arg Met Tyr Lys
            165             170             175

Ala Lys Glu Met Lys Val Pro Tyr Phe Ser Leu Ser
            180             185
```

DIGUANYLATE CYCLASE METHOD OF PRODUCING THE SAME AND ITS USE IN THE MANUFACTURE OF CYCLIC-DI-GMP AND ANALOGUES THEREOF

CROSS-REFERENCE TO RELATED APPLICATIONS

This application is a U.S. National Stage application of International Application No. PCT/SG2010/000060 filed Feb. 18, 2010 and claims benefit of and priority from, U.S. provisional patent application No. 61/156,826, filed on Mar. 2, 2009, the contents of both are hereby incorporated herein by reference.

FIELD OF THE INVENTION

A novel diguanylate cyclase, the method of making the same and its uses in the production of cyclic Di-GMP and cyclic-di-GMP analogues.

BACKGROUND OF THE INVENTION

C-di-GMP, or Bis-(3'-5')-cyclic dimeric guanosine monophosphate (cyclic-di-GMP or c-di-GMP), is a second messenger found in bacteria for intracellular signal transduction. Accumulating evidence suggest that c-di-GMP regulates a wide variety of bacterial behaviors such as biofilm formation, motility and virulence expression. The critical role of c-di-GMP in biofilm formation and virulence expression indicated that c-di-GMP may play vital roles in the chronic and acute infection caused by some pathogenic bacteria. The cyclic-di-GMP is a widespread bacterial messenger molecule with potential application as therapeutic agent for treating bacterial infection. Potential applications of cyclic-di-GMP and its analogues as a therapeutic agent include: Inhibiting colonization and biofilm formation by S. aureus; inhibiting proliferation of human colon carcinoma cells; an immunomodulatory molecule and has potent effects on antibody production and for preventing biofilm formation or promoting biofilm dispersal in medical equipment and devices such as lung inhalers, heart stents, heart valves; enteral tubing and the like.

Given the increasingly evident correlation between c-di-GMP signaling and bacterial pathogenesis, there is strong interest in the microbiology community to identify and characterize the components of c-di-GMP signaling network. Meanwhile, the use of c-di-GMP directly as a therapeutic agent for treating bacterial infection is also being explored. It was reported that exogenous c-di-GMP can reduce in vitro cell-cell interactions and biofilm formation of the gram-positive pathogen Staphylococcus aureus, including human methicillin-resistant S. aureus strains and animal clinical isolates. C-di-GMP was found to inhibit colonization and biofilm formation by S. aureus in a murine model of mastitis infection, resulting in the enhanced ability of the host to clear the pathogen. It was shown that c-di-GMP can modulate host cellular responses by inhibiting basal and growth factor-induced proliferation of human colon carcinoma cells. Studies also suggested that c-di-GMP is an immunomodulatory molecule with potent immunoprophylactic properties and vaccine adjuvant effects on antibody production.

Biochemical characterization of the macromolecules involved in c-di-GMP signaling, including the enzymes and receptors, requiring the use of c-di-GMP as substrate or ligand for biochemical assay. C-di-GMP can also be used as starting material for the synthesis of c-di-GMP analogues to be used as chemical probes or inhibitors. Although C-di-GMP could be obtained directly from bacterial cells, the low intracellular concentration of c-di-GMP makes this approach impractical for c-di-GMP production.

Cyclic di-GMP is synthesized by proteins with diguanylate cyclase activity. These proteins typically have a characteristic GGDEF motif, which refers to a conserved sequence of five amino acids. The GGDEF motif is housed within a GGDEF domain that has been observed in 681 bacteria species. Information on the domain can be found at the Pfam protein families database (http://pfam.sanger.ac.uk/family?acc=PF00990). Current enzymatic synthesis of c-di-GMP using known diguanylate cyclases (DGC) protein suffers from low production yield. Cyclic di-GMP is also an allosteric inhibitor of cellulose synthase in Gluconacetobacte. xylinus. C-di-GMP has been found to function in many bacteria as evidenced by the presence of large number of GGDEF, EAL and HD-GYP domain-containing proteins. GGDEF domains function as diguanylate cyclases (DGC) that catalyze the synthesis of c-di-GMP from GTP, whereas EAL and HD-GYP domains function as phosphodiesterases (PDE-A) for degrading c-di-GMP.

Currently, c-di-GMP is synthesized chemically or enzymatically in small quantity in research laboratories. The solution and solid-phase chemical synthesis approaches are expensive and time-consuming given the multi-step nature of the synthetic routes. On the other hand, the enzymatic production of c-di-GMP by using DGC domain-containing proteins only involves a single condensation of two GTP molecules. The enzymatic approach has been employed by several labs for the production of c-di-GMP for biochemical assays by using WspR, PleD or VCA0956, three mesophilic DGC domain-containing proteins from Pseudomonas aeruginosa, Caulobacter crescentus and Vibrio cholerae respectively. Previously, we found that the preparation of c-di-GMP by using mesophilic DGC proteins such as WspR only yielded limited amount of c-di-GMP.

DGC proteins are known to be tightly regulated by cellular c-di-GMP concentration. It is theorised that this regulation involves the I-site in PleD. The crystal structures of PleD and WspR have revealed that the I-site contains a RXXD motif.

There is intense current interest in c-di-GMP, and analogues, because of its role as a bacterial signalling molecule and its importance in bacterial virulence, pathogenesis, and biofilm formation. As a major focus of research and development there is a need to produce large volumes of c-di-GMP, or analogues. One of the major limitations of using well known DGC proteins such as WspR and PA290 for c-di-GMP production is the significant loss of enzymatic activity during c-di-GMP preparation. The currently available methods are not sufficient, producing only limited amounts of c-di-GMP. Access to large quantity of cyclic-di-GMP is prerequisite for the development of the molecule as an antibacterial agent. Previous methods used for synthesizing cyclic-di-GMP are too costly or time/labor consuming for this purpose.

SUMMARY

One aspect of the invention provides a diguanylate cyclase polypeptide comprising a GGDEF motif and an I-site wherein at least one of the conserved amino acids, arginine or aspatic acid of the I-site is replaced with a neutral amino acid forming a mutant diguanylate cyclase that does not bind c-di-GMP.

Preferably the neutral amino acid is either a non-polar amino acid or an uncharged polar amino acid. In one embodiment the non-polar amino acid is alanine. In one embodiment the uncharged polar amino acid is glutamine.

In a preferred embodiment the diguanylate cyclase polypeptide comprises an amino acid sequence at least 90% homologous to a diguanylate cyclase polypeptide comprising a GGDEF motif isolated from a thermophilic bacteria. Preferably the thermophilic bacteria is selected from *Thermotoga maritime; Thermoanaerobacter ethanolicus; Thermoanaerobacter tengcongensis; Fervidobacterium nodosum; Thermosipho melanesiensis; thermotoga petrophila;* or *Moorella thermoacetica*. In one emdodiment the thermophilic bacteria is *Thermotoga maritime*.

Preferably the mutant diguanylate cyclase comprises a monomer in solution.

In a preferred embodiment the mutant diguanylate cyclase comprises a sequence of SEQ ID NO.: 2 or SEQ ID NO. 3, or SEQ ID NO. 3

In one embodiment the diguanylate cyclase is coupled to a support. In one embodiment the support is a sol-gel.

Another aspect of the invention provides a polynucleotide capable of expressing a mutant diguanylate cyclase polypeptide comprising a GGDEF motif and an I-site wherein at least one of the conserved amino acids, arginine or aspatic acid of the I-site is replaced with a neutral amino acid. One embodiment includes the sequence of SEQ ID NO. 1.

Another aspect of the invention provides an expression vector comprising the polynucleotide of the invention operably linked to a regulatory sequence capable of directing expression of said polynucleotide in a host cell.

Another aspect of the invention provides a method of producing a mutant diguanylate cyclase polypeptide of the invention that does not bind c-di-GMP. In one embodiment the mutant diguanylate cyclase polypeptide is synthesized chemically. In another embodiment the mutant diguanylate cyclase polypeptide is produced in the expression vector of the invention with the polynucleotide of the invention.

Another aspect of the invention provides a method of manufacturing cyclic-di-GMP or cyclic-di-GMP analogues comprising the steps of: a) incubating the mutant diguanylate cyclase polypeptide of the invention with Guanosine-5'-triphosphate; and b) isolating the cyclic-di-GMP or cyclic-di-GMP analogues.

In one embodiment the analogue comprises 6-thio cyclic-di-GMP. In another embodiment the analogue comprises 32P-radioisotope-labelled cyclic-di-GMP.

Another aspect of the invention provides an analogue manufactured by the method of the invention comprising the formula:

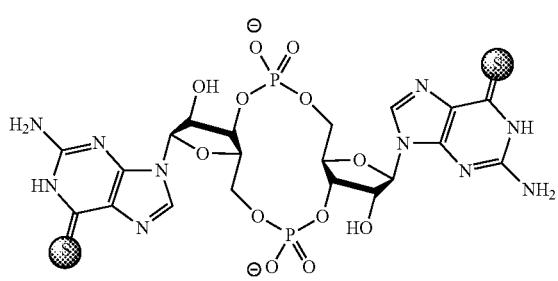

DETAILED DESCRIPTION

Figure 1:
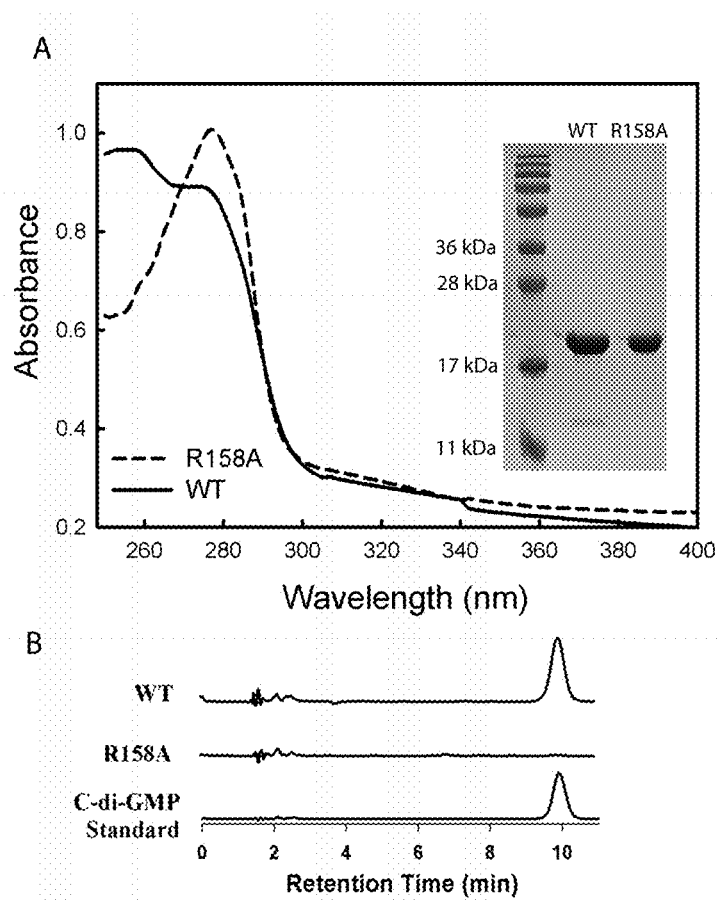
FIG. 1. Characterization of tDGC and mutant R158A. A. Absorption spectra of tDGC and the mutant R158A. Inset: SDS-PAGE gel of wild type and mutant tDGC. B. HPLC analysis of the supernatant from the denaturation of tDGC and mutant R158A.

Here we report a new stand-alone diguanylate cyclase polypeptide having a GGDEF motif and an I-site of RXXD wherein at least one of the conserved amino acids, arginine or aspatic acid is replaced with a neutral amino acid forming a mutant diguanylate cyclase that does not bind to c-di-GMP and therefore is not allosterically inhibited by c-di-GMP. The neutral amino acid could be any one of the non-polar amino acid such as alanine, glycine, valine, leucine, isoleucine, Proline, phenylalanine or tryptophan. Alternatively the neutral amino acid could be an uncharged polar amino acid such as Cysteine, Glutamine, histidine, serine, threonine or tyrosine. Preferably the non-polar amino acid is alanine. Preferably the polar amino acid is glutamine. We demonstrate that the product inhibition could be substantially alleviated by mutation of a key amino acid residue in the putative c-di-GMP-binding site. The c-di-GMP product inhibition that severely limited production yield was significantly alleviated by mutation of a conserved residue in the putative regulatory I-site.

In one embodiment the diguanylate cyclase polypeptide is thermophilic with significantly improved thermostability in comparison with other mesophilic DGC proteins. With improved thermostability and suppressed product inhibition, we were able to readily produce hundreds of milligrams of c-di-GMP by using the optimized procedures for enzymatic reaction and product purification. Considering the poor thermostability of mesophilic DGC proteins, we reasoned that a thermophilic DGC protein would be more suitable for c-di-GMP production. We searched the genomes of all the thermophilic microorganisms available in the DOE microbial genomics database (http://microbialgenomics.energy.gov/) for GGDEF domain proteins. Among the identified GGDEF domain proteins, the proteins that lack the intact GGDEF or GGEEF motif were excluded for consideration.

Mutant Diguanylate Cyclase Polypeptides

Mutant diguanylate cyclase polypeptides of the present invention have about 200 to 300 amino acids, encode a diguanylate cyclase able to synthesis c-di-GMP in large volumes. The mutant diguanylate cyclase polypeptides also comprise a GGDEF motif and an I-site of RXXD within a GGDEF domain wherein at least one of the conserved amino acids, arginine or aspatic acid is replaced with a neutral amino acid. Mutant diguanylate cyclase polypeptides of the invention also include fragments and derivatives of diguanylate cyclase polypeptides that comprise a GGDEF motif; an 1-site of RXXD wherein at least one of the conserved amino acids, arginine or aspatic acid is replaced with a neutral amino acid and retain the function of synthesising c-di-GMP. Particularly fragments or derivatives have substantially the same biological activity of synthesising c-di-GMP and the mutated I-site does not bind c-di-GMP. The polypeptides can be prepared by recombinant or chemical synthetic methods. Presently preferred mutant diguanylate cyclase polypeptides include those comprising the amino acid sequence of SEQ ID NOS: 2, 3, 4 or variants or homologues, including fragments, thereof. A preferred polypeptide consists of amino acids 1 to 188 of the amino acid sequence shown as SEQ ID NO: 2, 4 or variants, homologues or fragments, thereof. A preferred polypeptide consists of amino acids 1 to 160 of the amino acid sequence shown as SEQ ID NO: 3 or variants, homologues or fragments, thereof.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID. Nos 2, 3 or 4. In particular, homology should typically be considered with respect to those regions of the sequence known to be essential for the function of the enzyme rather than non-essential neighbouring sequences. Thus, for example, homology comparisons are preferably made over regions corresponding to the GGDEF domain and/or the mutation at the I-site of the amino acid sequence set out in SEQ ID NOS: 2, 3 or 4. The GGDEF domain corresponds to approximately amino acids 88 to 241 of the natural thermophilic TM1788 isolated from *Thermotoga maritime* which corresponds approximatly to amino acids 24 to 181 SEQ ID NOS: 2 and 4. The GGDEF domain corresponds to approximately amino acids 1 to 160 of SEQ ID NO: 3. The GGDEF motif corresponds to approximately amino acids 107 to 111 of SEQ ID NOs: 2 and 4 and approximately amino acids 83 to 87 of SEQ ID NO: 3. The mutated I-site corresponds to approximately amino acids 98 to 101 of SEQ ID NOS: 2 and 4. The mutated I-site corresponds to approximately amino acids 74 to 77 of SEQ ID NO: 3. Preferred polypeptides of the invention comprise a contiguous sequence having greater than 50, 60 or 70% homology, more preferably greater than 80 or 90% homology, to one or more of amino acids 24 to 181 or 107 to 111 or 98 to 101 (where it contains a neutral amino acid) of SEQ ID NO: 2, 4 or the corresponding regions of SEQ ID NO: 3. Preferred polypeptides may alternatively or in addition comprise a contiguous sequence having greater than 80 or 90% homology, to amino acids 24 to 181 of SEQ ID NOS: 2 or 4 or the corresponding region of SEQ ID NO: 3.

Although homology can also be considered in terms of similarity (i.e. amino acid residues having similar chemical properties/functions), in the context of the present invention it is preferred to express homology in terms of sequence identity. The terms "substantial homology" or "substantial identity", when referring to polypeptides, indicate that the polypeptide or protein in question exhibits at least about 70% identity with an entire biologically active protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate percentage homology (% homology) between two or more sequences.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly includes the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package, FASTA and the GENEWORKS suite of comparison tools. Both BLAST and FASTA are available for offline and online searching. However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Mutant diguanylate cyclase polypeptide homologues include those having the amino acid sequences, wherein one or more of the amino acids is substituted with another amino acid which substitutions do not substantially alter the biological activity of the GGDEF motif or the mutated I-site. A mutant diguanylate cyclase polypeptide homologue according to the invention preferably has 80 percent or greater amino acid sequence identity to the amino acid sequence set out in SEQ ID NOS: 2 or 4. Examples of mutant diguanylate cyclase polypeptides homologues within the scope of the invention include the amino acid sequence of SEQ ID NOS: 2 or 4 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

"Mutant diguanylate cyclase enzyme" or "Mutant diguanylate cyclase polypeptide" refers to a protein or polypeptide encoded by the gene sequence encoding a GGDEF motif and an I-site of RXXD wherein at least one of the conserved encoded amino acids, arginine or aspatic acid is replaced with a neutral acid. Preferably the gene sequence encodes a GGDEF domain. Preferably the gene sequence encoding a mutant diganylate cyclise polypeptide is that set out in SEQ ID NO: 1, variants or fragments thereof. Also included are proteins encoded by DNA that hybridize under high or low stringency conditions, to DNA encoding nucleic acids and closely related polypeptides or proteins retrieved by antisera to the Mutant diguanylate cyclase polypeptides.

"Protein modifications or fragments" are provided by the present invention for Mutant diguanylate cyclase polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

In addition to the similarity of function, the modified polypeptide may have other useful properties, such as a longer half-life. The similarity of function (activity) of the modified polypeptide may be higher than the activity of the wild-type diguanylate cyclase polypeptide. The function/biological activity of homologues, variant, derivatives or fragments relative to diguanylate cyclase polypeptides may be determined, for example, by means of biological assays. For example, when incubated with Guanosine-5'-triphosphate (GTP), mutant diguanylate cyclase polypeptide converts at least 10 to 80% of the GTP to c-di-GMP. Thus one test for mutant diguanylate cyclase polypeptide activity is to incubated it with GTP and determine whether a large amount of c-di-GMP is formed. Another test for mutant diguanylate cyclase polypeptide is to determine if c-di-GMP binds to the mutant diguanylate cyclase polypeptide at the I-site. Preferred mutant diguanylate cyclase polypeptide, homologues, variants and fragments will not bind to c-di-GMP. Another test for mutant diguanylate cyclase polypeptide is to determine if the mutant diguanylate cyclase polypeptide exits as a monomer in solution. Preferred mutant diguanylate cyclase polypeptide, homologues, variants and fragments exist as a monomer in solution.

The modified polypeptide may be synthesized using conventional techniques, or is encoded by a modified nucleic acid and produced using conventional techniques. The modified nucleic acid is prepared by conventional techniques. A nucleic acid expressing a polypeptide with a function substantially similar to the modified protein described above.

Besides substantially full-length polypeptides, the present invention provides for biologically active fragments of the polypeptides. Significant biological activities include synthesis of c-di-GMP and no binding to c-di-GMP.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels (sol gel), cells, or other substrates. Such supports may take the form, for example, of beads, wells, dipsticks, or membranes.

In one embodiment the mutant diguanylate cyclase enzyme is trapped in a Sol-Gel matrix by using a mild condition that prevents the enzyme from denaturation during immobilization. Sol-Gel beads with the mutant diguanylate cyclase enzyme trapped inside are then prepared. The enzyme inside the beads is active in synthesizing cyclic-di-GMP and highly stable with a shelf lifetime of months. The entrapment of the mutant diguanylate cyclase enzyme in Sol-Gel has proven to be a useful method for improving the efficiency of cyclic-di-GMP synthesis and reducing production cost.

The present invention also provides for fusion polypeptides, comprising mutant diguanylate cyclase polypeptides and fragments. Homologous polypeptides may be fusions between two or more mutant diguanylate cyclase polypeptide sequences or between the sequences of mutant diguanylate cyclase polypeptide and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion proteins will typically be made by either recombinant nucleic acid methods, as described below, or may be chemically synthesized.

"Protein purification" refers to various methods for the isolation of the mutant diguanylate cyclase polypeptides from other biological material, such as from cells transformed with recombinant nucleic acids encoding mutant diguanylate cyclase polypeptide, and are well known in the art. For example, such polypeptides may be purified by immuno-affinity chromatography employing, e.g., the antibodies specific to mutant diguanylate cyclase polypeptide. Various methods of protein purification are well known in the art.

The terms "isolated", "substantially pure", and "substantially homogeneous" are used interchangeably to describe a protein or polypeptide that has been separated from components that accompany it in its cellular state. A monomeric protein is substantially purified when at least about 60 to 75% of a sample exhibits a single polypeptide sequence. A substantially purified protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for application.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

Peptides of the invention may be synthesized chemically using known techniques such as liquid phase synthesis or solid phase synthesis such as t-BOC or Fmoc, or BOP SPPS or any chemical synthesis method known to those in the art. Alternatively the peptide may be made biologically within a cell or vector designed to use the machinery of translation and/or transcription for peptide synthesis.

Nucleic Acid Constructs and Vectors

According to the invention there is provided an isolated diguanylate cyclase nucleic acid molecule which molecule typically encodes a diguanylate cyclase polypeptide, comprising a GGDEF motif and an I-site of RXXD, variant, or analog, including fragments, thereof. This nucleic acid molecule may then be mutated to obtain the Mutant diguanylate cyclase nucleic acid molecule of the invention. The Mutant diguanylate cyclase nucleic acid molecule of the invention expresses a mutant diguanylate cyclase polypeptides that comprise a GGDEF motif; an I-site of RXXD wherein at least one of the conserved amino acids, arginine or aspatic acid is replaced with a neutral amino acid. The mutation may be achieved by site directed mutagenisis or any other mutation methods known in the art. Specifically provided are DNA molecules for use in securing expression of a mutant diguanylate cyclase polypeptides capable of synthesising c-di-GMP without binding to c-di-GMP. The DNA molecule may comprise (a) that set out in SEQ ID NO: 1 or fragments thereof; (b) DNA molecules that hybridize to the DNA molecules defined in (a) or hybridisable fragments thereof; and (c) DNA molecules that code on expression for the amino acid sequence encoded by any of the foregoing DNA molecules.

Preferred DNA molecules according to the invention include DNA molecules comprising the sequence set out in SEQ ID NO: 1 or fragments thereof.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

An "isolated" or "substantially pure" nucleic acid (e.g., an RNA, DNA or a mixed polymer) embraces a nucleic acid sequence or protein that has been removed from its naturally occurring environment, and includes recombinant or cloned DNA isolates and chemically synthesized analogs or analogs biologically synthesized by heterologous systems.

Polynucleotides of the invention may be incorporated into a recombinant replicable vector for introduction into a prokaryotic host. Such vectors may typically comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed.

An appropriate promoter and other necessary vector sequences will be selected so as to be functional in the host, and may include, when appropriate, those naturally associated with diguanylate cyclase genes. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Vectors and promoters suitable for use may be joined to an amplifiable gene so that multiple copies of the gene may be made. For appropriate enhancer and other expression control sequences.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Thus the present invention provides host cells transformed or transfected with a nucleic acid molecule of the invention. Large quantities of the nucleic acids and polypeptides of the present invention may be prepared by expressing the mutant diguanylate cyclase nucleic acids or portions thereof in vectors or other expression vehicles in compatible prokaryotic host cells. The most commonly used prokaryotic hosts are strains of *Escherichia coli*, although other prokaryotes, such as *Bacillus subtilis* or *Pseudomonas* may also be used.

Thus, the present invention also provides methods for preparing a mutant diguanylate cyclase polypeptide comprising: (a) culturing a cell as described above under conditions that provide for expression of the mutant diguanylate cyclase polypeptide; and (b) recovering the expressed mutant diguanylate cyclase polypeptide. This procedure can also be accompanied by the steps of: (c) chromatographing the polypeptide using any suitable means known in the art; and (d) purifying the polypeptide by for example gel filtration.

Prokaryotic or eukaryotic cells transformed with the polynucleotides of the present invention will be useful for the production of the nucleic acids and polypeptides of the present invention.

Use of Mutant Diguanylate Cyclase Polypeptides in the Production of c-di-GMP and c-di-GMP Analogues Mutant diguanylate cyclase polypeptides of the invention are incubated with GTP in appropriate conditions to synthesis c-di-GMP or analogues. After more than 80% of GTP is converted to c-di-GMP or analogues, fresh GTP is supplemented. Approximately about 8 to 15 batches of GTP may be added. After the reaction, the protein is precipitated and removed. Further purification may be used to obtain high quality c-di-GMP or c-di-GMP or analogues. Preferably the c-di-GMP are lyophilized to yield the white powder for easy shipping and use.

Here we report the overexpression and characterization of a stand-alone thermophilic diguanylate cyclase domain (tDGC) protein with enhanced thermostability. The mutated thermophilic DGC protein can be used for efficient production of c-di-GMP by using standard equipment in biochemistry laboratories. The enzyme can be used for synthesis of radio-isotope labeled c-di-GMP for enzymatic and binding assays. The easy access to c-di-GMP shall encourage the synthesis of structural analogues by chemical modification of c-di-GMP as potential inhibitors and chemical probes.

The mutant diguanylate cyclase polypeptide is produced as described above however the diguanylate cyclase polypeptide is selected from a thermophilic bacteria prior to mutating the I-site. With the mutant thermophilic DGC, we demonstrated that hundreds of milligrams of c-di-GMP can be readily prepared by using the optimized procedures for enzymatic reaction and product purification. The thermophilic enzyme will be a valuable tool for other research laboratories for c-di-GMP synthesis as well as the preparation of c-di-GMP derivatives.

EXAMPLES OF EMBODIMENTS

Selection of Thermophilic Diguanylate Cyclase Protein

We have identified quite a number of the thermophilic DGC proteins from the following bacteria: *Thermotoga maritime; Thermoanaerobacter ethanolicus* X514; *Thermoanaerobacter tengcongensis; Fervidobacterium nodosum* RT17-B1; *Thermosipho melanesiensis* B1429; *thermotoga petrophila* rku-1; and *Moorella thermoacetica*. Several of the thermophilic DGC proteins examined by us are listed in table 1. The most successful thermophilic DGC protein was a GGDEF domain-containing protein (TM 1788) isolated from *Thermotoga maritime*.

TABLE 1 thermophilic DGC proteins tested

| Species | Uniprot accession Number | Entry name | diguanylate cyclase residue length |
|---|---|---|---|
| *Thermosipho melanesiensis* BI429 | A1GLW7 | A1GLW7_9THEM | 197 |
| *thermosipho melanesiensis* bi429 | A1GMY9 | A1GMY9_9THEM | 305 |
| *thermotoga petrophila* rku-1 | A1GHU7 | A1GHU7_9THEM | 450 |
| *thermotoga petrophila* rku-1 | A1GI95 | A1GI95_9THEM | 258 |
| *thermotoga petrophila* rku-1 | A1GJF1 | A1GJF1_9THEM | 290 |
| *Thermotoga maritima* | Q9X2A8 | Q9X2A8_THEMA | 248 |

A GGDEF domain-containing protein (TM1788) from *Thermotoga maritima* was selected after the evaluation of the possibility of producing soluble protein by using bioinformatic tools. The 241 amino acid long TM1788 was predicted to contain a single GGDEF domain (88-241aa) with an N-terminal segment (1-86) that contains a few strings of hydrophobic residues. We named this tDGC.

Designing a Mutation in the I-Site

Figure 2:
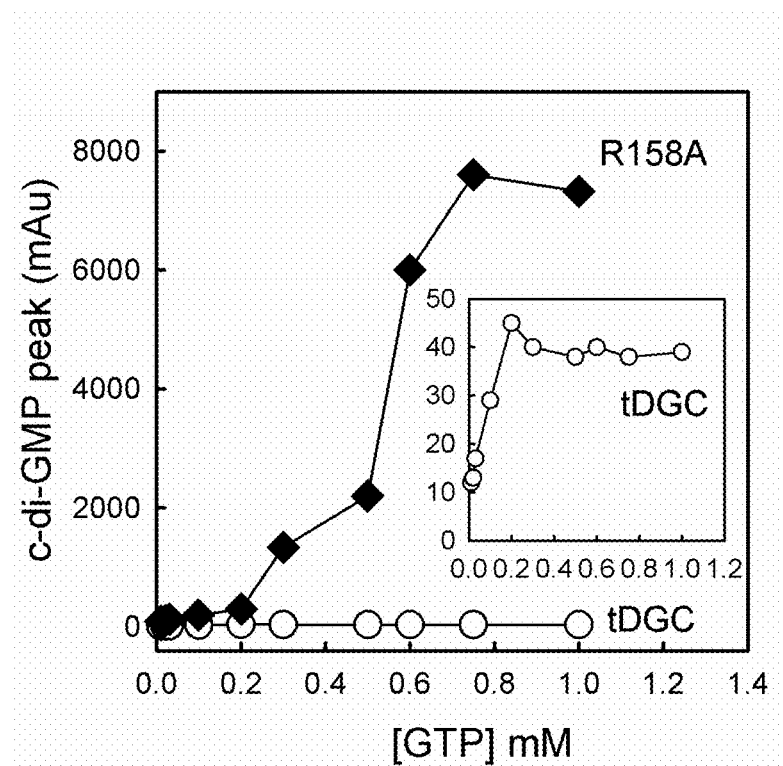
FIG. 2. Comparison of the synthesis of c-di-GMP at various substrate concentrations for tDGC and the R158A mutant. Inset: Substrate concentration dependence of tDGC activity. Conditions: 50 mM Tris-Cl (pH 8.0), 20 mM $MgCl_2$, 250 mM NaCl, 10 μM enzyme, 1 mM DTT, 55° C.
Figure 3:
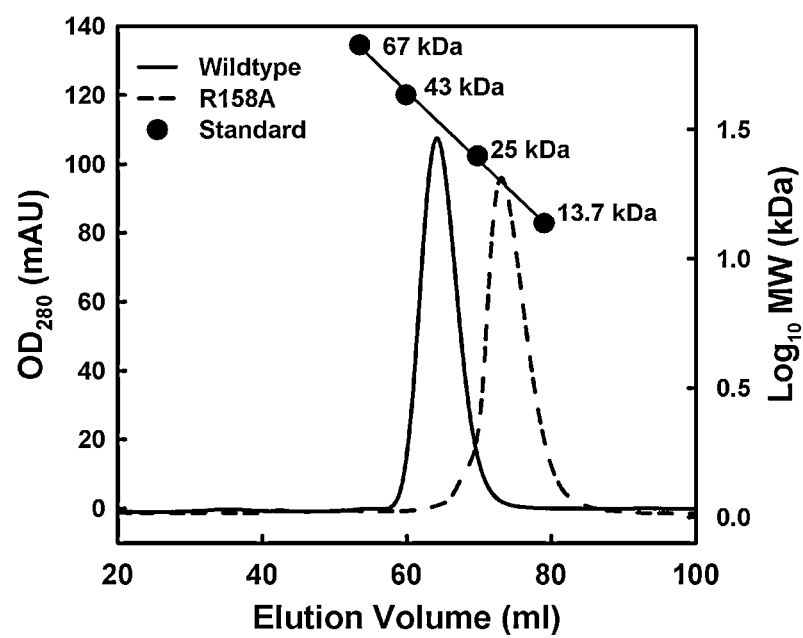
FIG. 3. Characterization of tDGC and the R158A mutant by size-exclusion chromatography.

Examination of the sequence and structural model of tDGC suggested that tDGC contains a $R^{158}RSD^{161}$ motif, and thus, likely to contain an intact I-site. Given the presence of the conserved RXXD motif and the observation that tDGC binds c-di-GMP tightly we subsequently tested whether mutation of one or more of the residues in the I-site might be able to eliminate product inhibition without affecting protein stability and folding. The best result was observed for the mutant R158A. We observed that the absorption spectrum of the R158A mutant did not exhibit a 256 nm peak, indicating that c-di-GMP is no longer associated with the protein (FIG. 1). Importantly, the mutant enzyme was capable of turning over almost 100% of the GTP substrate into c-di-GMP under the assay conditions, suggesting the weakening of product inhibition after the mutation. Enzymatic assay shows that the production yield for the mutant is much higher than tDGC at various GTP concentrations (FIG. 2). Steady-state kinetic measurement showed that the R158A mutant catalyzed the GTP condensation with a $k_{cat}$ of 2.6 min$^{-1}$ at 55° C. The production yield decreased after GTP reached ca. 0.8 mM, suggesting inhibition of enzymatic activity at high substrate concentration, in comparison with the lower substrate inhibition concentration (100 μM) for the wild type tDGC. Interestingly, we found that the mutant enzyme appeared to exist in solution as a monomer, in contrast to the dimer form for tDGC (FIG. 3). The observation was surprising since the synthesis of c-di-GMP from two molecules of GTP requires the DGC protein to function in its dimeric form. The observation indicated that the binding of C-di-GMP at the I-site plays a critical role in stabilizing the dimeric form, and that the synthesis of c-di-GMP is achieved by the formation of transient dimer by the protein in solution. Together, the observations suggested that the R158A mutation considerably weakened product inhibition without causing significant decrease in protein stability, and thus, the R158A mutant is more suitable for c-di-GMP synthesis.

Cloning and Site-Directed Mutagenesis

Considering that the hydrophobic motifs might affect protein solubility, a gene construct that encodes the stand-alone GGDEF domain (82-241 amino acid, referred as tDGC) was custom synthesized with the gene sequence optimized for *E. coli* overexpression. A gene construct encoding the C-terminus of the TM1788 gene was commercially synthesized by GenScript Inc, amplified by PCR, and cloned into the expression vector pET28b(+) (Novagen) between the NdeI and XhoI restriction sites. The plasmid harboring the gene construct and the (His)$_6$-Tag encoding sequence was transformed into *E. coli* strain BL21(DE3). Mutants were generated using the Site-Directed Mutagenesis II Kit (Stratagene) according to the manufacturer's instruction manual. Mutations were verified using BigDye Terminator v3.1 Cycle Sequencing Kit on ABI Prism 3100 Genetic Analyzer (Applied Biosystems). Cell stocks were stored in 20% glycerol at −80° C.

The gene construct was subsequently cloned into the pET28b(+) expression vector and transformed into BL21 (DE3) *E. coli* strain for protein expression. After optimization of expression conditions, the majority of the protein could be expressed as soluble protein in reasonably high yield (12-15 mg per liter culture) with a small fraction observed in inclusion body.

Mutant Variations

Given that a positively charged Arginine was replaced with a neutral uncharged alanine we hypothesised that replacement of the positively charged Arginine by any neutral amino acid residues would abolish the c-di-GMP binding capability. To test this we replaced the arginine with a glutamine R158Q. Both the R158A (SEQ ID NO.: 2) and the R158Q (SEQ ID NO.: 4) mutants abolished the c-di-GMP binding capability.

Protein Expression and Purification

For protein expression, 2 ml of inoculum from the cell stock was added to one liter of LB medium. Bacterial culture was grown at 37° C. up to OD=0.8 before being induced with 0.8 mM IPTG at 25° C. for 4 hours. After centrifugation, the pellets were lysed in 20 ml lysis buffer that contains 50 mM Tris-Cl (pH 8.0), 300 mM NaCl, 5% glycerol, 1% (3-mercaptoethanol and 1 mM PMSF. After centrifugation at 25,000 rpm for 30 min, the supernatant was filtered and then incubated with 2 ml of Ni$^{2+}$-NTA resin (Qiagen) for 30 min at 4° C. The resin was washed with 50 ml of W1 buffer (lysis buffer with 20 mM imidazole) and 20 ml of W2 buffer (lysis buffer with 50 mM imidazole). The proteins were eluted using a stepped gradient method with the elution buffer containing 20 mM Tris (pH 8.0), 200 mM NaCl, 5% glycerol and 200, 300 and 500 mM imidazole. After SDS-PAGE gel analysis, fractions with purity higher than 95% were pooled together and further purified using size-exclusion chromatography.

The absorption spectrum of the protein exhibited an extra peak at 256 nm in addition to the 278 nm protein peak (FIG. 1A). HPLC analysis of the protein solution after thermal denaturation suggested that the 256 nm peak is due to a tightly associated c-di-GMP ligand (FIG. 1B). Enzymatic assay showed that the stand-alone domain was enzymatically active by generating c-di-GMP when incubated with GTP and Mg$^{2+}$ ion. The enzyme showed significantly enhanced stability compared to WspR and PA290 based on the observation that the enzyme was active after several days of incubation at 30° C. However, despite the improved thermostability, we found the overall production yield was low even at high substrate concentration with prolonged incubation.

Size-Exclusion Chromatography

Gel filtration was performed at 4° C. using the AKTA FPLC system equipped with a Superdex 75 HR 16/60 column (Amersham Biosciences). The buffer used for gel filtration is comprised of 50 mM Tris-Cl (pH 8.0), 300 mM NaCl, 5% Glycerol, 1 mM DTT. Fractions containing the recombinant protein were concentrated using Amicon concentrator (Millipore) to a final concentration of ca. 5 mg/ml as measured using Bradford assay. Concentrated proteins were stored in −80° C. degree after flash-freeze using liquid nitrogen. Mutant proteins were expressed, purified and stored following the same procedure. The molecular weight and oligomeric state of the protein was estimated based on the standard curve generated by using the standard proteins that include albumin, ovalbumin, chemotrypsinogen, RNase A. The final yield of the recombinant protein was 12-15 mg per liter culture for the wild type the mutant enzyme.

Diguanylate Cyclase (DGC) Activity Assay Optimization and Steady-State Kinetic Measurement Enzyme assays were conducted to determine the optimal salt concentration of the DGC reaction, with the buffer that contains 50 mM Tris-HCl (pH 8.0), 20 mM MgCl$_2$, 100 µM GTP, 10 µM Enzyme, and 0-500 mM NaCl. Enzyme assays were conducted to determine the optimal pH concentration of the DGC reaction, with the buffer that contains 50 mM Tris-HCl (pH 7.0-9.0), 250 mM NaCl, 20 mM MgCl$_2$, 100 µM GTP, 10 µM Enzyme. Reaction mixtures were incubated in a waterbath at 55° C. for 15 minutes. After heating at 95° C. for 10 min and centrifugation at 14,000 rpm for 5 min to remove protein precipitate, the supernatant was filtered before loading onto the Eclipse XDB-C18 (4.6×150 mm) column for monitoring the turnover from GTP to c-di-GMP using an Agilent LC1200 system (Mobile phase: 20 mM Triethylammonium bicarbonate (pH 7.0, pH adjusted using acetic acid), 9% Methanol, Flow rate: 1 mL/min). For thermostability analysis, the mutant protein was incubated at 45, 55 and 65° C., aliquots of protein solution were taken out at different time points to add into the reaction mixture that contains 50 mM Tris-Cl (pH 7.5), 250 mM NaCl, 20 mM MgCl$_2$ and 100 µM GTP. The reaction was allowed to last for 10 min before being stopped and analyzed for GTP turnover by using HPLC. For product yield and steady state kinetic measurement, the standard reaction mixture include 50 mM Tris-Cl (pH 8), 20 mM MgCl$_2$, 300 mM NaCl, 1 µM Enzyme, 5-800 µM GTP. Reactions were incubated at 55° C. for 1-60 minutes to obtain linear range of progress. For steady kinetics, data was fitted using GraphPad (Prism) to obtain the kinetic parameters.

Figure 4:
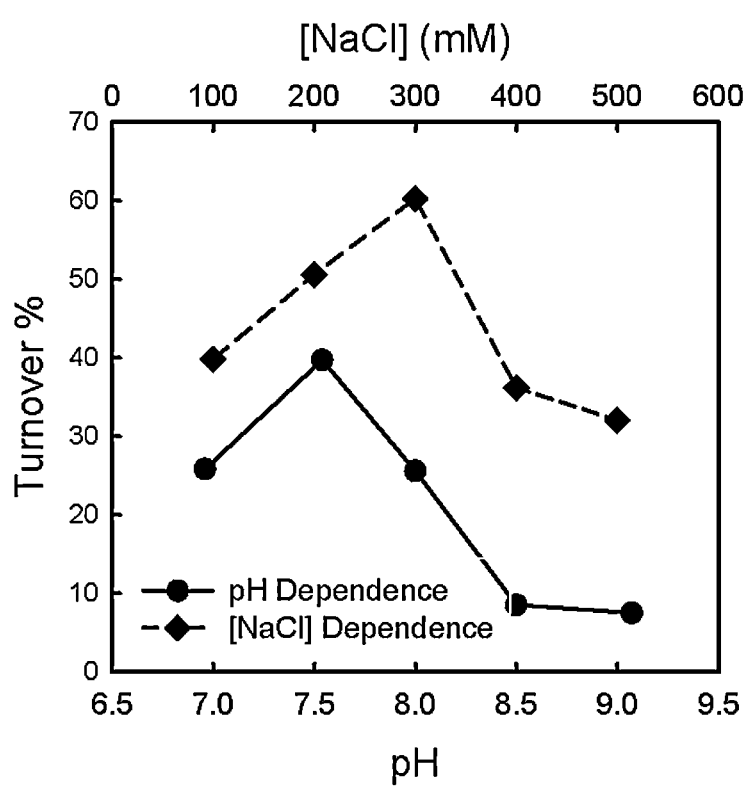
FIG. 4. pH and salt dependence of enzymatic activity of mutant R158A. Assay conditions were described in Material and Methods.
Figure 5:
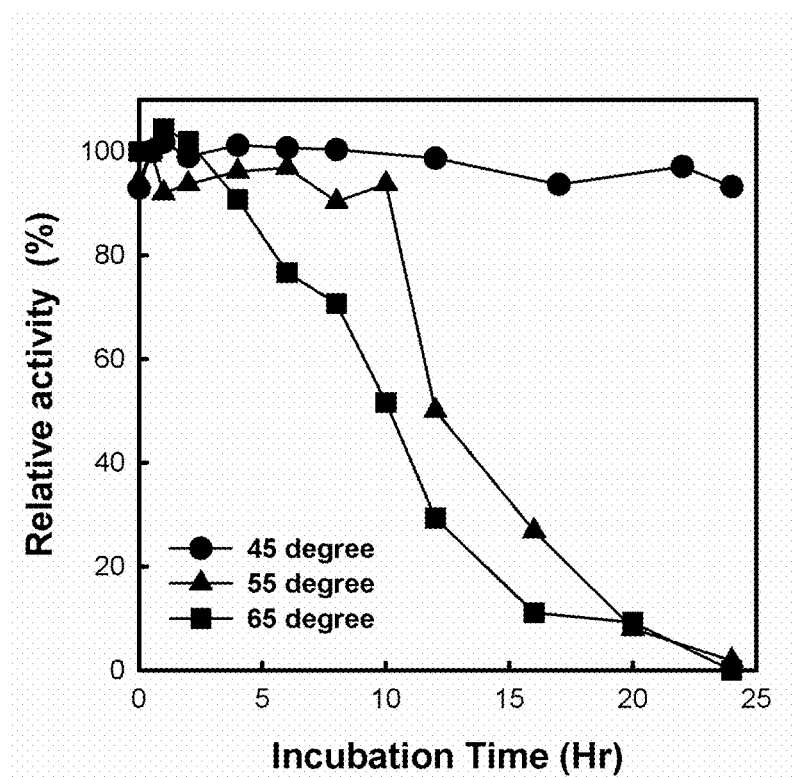
FIG. 5. Analysis of the thermostability of R158A mutant. The production yield was normalized to the highest production yield at zero time point. Assay conditions are described in Material and Methods.

Systematic screening of pH, salt and temperature was carried out to optimize the reaction conditions for the mutant tDGC. The enzyme was found to be most efficient at pH 7.5 and at relatively high salt conditions (250-300 mM NaCl) (FIG. 4). Thermostability analysis showed that the activity of the enzyme drops slowly with time at elevated temperature (45, 55 and 65° C.), with an extended half-lifetime of more than 25 hours at 45° C. (FIG. 5).

Large Scale Preparation and Product Purification

C-di-GMP was synthesized by incubating the R158A mutant and GTP (Sigma, Cat No: G8877) at 45° C. in a 30 or 50 ml reaction mixture that contains 50 mM Tris buffer (pH 7.5), 250 mM NaCl, 20 mM MgCl$_2$, 0.75-1 mM GTP, 1 mM DTT and 5-10 µM mutant enzyme. After more than 95% of GTP was converted to c-di-GMP as estimated by HPLC analysis, fresh GTP (0.75-1 mM final concentration) was supplemented. A total of 8-15 batches of GTP were added in a period of ten hours. After the reaction, the protein was precipitated and removed by heat treatment and the supernatant was concentrated using a rotary evaporator (Eyela) with the waterbath temperature set at 45° C. The concentrated supernatant was loaded onto a semi-preparative Eclipse XDB-C18 (9.4×250 mm) column for purification by using the LC1200 system from Agilent. Sample injection and c-di-GMP peak collection was automated with an autosampler (Loading volume: 1 ml) and a fraction collector with 6 ml collecting vials. C-di-GMP was eluted using the same mobile phase described above with a flow rate of 3 mL/min. The fractions that contain c-di-GMP were pooled, concentrated by evaporation, and finally lyophilized to yield the white powder that was dissolved into 5 mM Tris buffer (pH 7.0) for storage at −20° C. The identity of the product was confirmed by MALDI-Mass spectrometry and comparison with standard from commercial source (Biolog, Germany). The extinction coefficient ($\epsilon_{260}$) of 26,100 OD $M^{-1}$ $cm^{-1}$ was used for the calculation of c-di-GMP concentration (15).

The R158A mutant protein and the optimized procedures enabled us to readily synthesize hundreds of milligrams of c-di-GMP with standard equipment found in biochemistry laboratories. For example, with 10 mg of the mutant enzyme, we were able to obtain more than 200 mg of c-di-GMP by adding multiple batches of substrate within a period of several hours. There should not be any difficulty to produce c-di-GMP on the scales of grams with more enzyme and longer reaction time. In comparison, the production yield with the mutant tDGC was significantly higher than that of WspR, considering that we could only obtain 10-20 mg of c-di-GMP with 50 mg of WspR previously (8). The produced c-di-GMP could be purified by using a HPLC system equipped with auto-sampler and fraction collector, and with the semi-preparative RP-C18 column and solvent system described in Materials and Methods. For production of c-di-GMP on the scales of grams, we would recommend a preparative HPLC system to shorten the preparation time. The final product in the form of white powder was obtained after the removal of HPLC solvent by using a lyophilizer or rotary evaporator.

Mutation of the I-Site of the Cytoplasmic Protein AxDGC2 from *Acetobacter xylinum*

The gene encoding AxDGC2 from *A. xylinum* was obtained from Genscript and was ligated into the pET-26(b þ)) vector (Novagen) between compatible restriction sites. The resulting plasmid was used as a template for PCR amplification of the isolated EAL domain (AxDGC2306-574) with the primers 5'-AAACATATGCGCAATCTGCGTGAACG-3' and 5'-AAACTCGAGCAGGGTAACGC-3'. The Expanded High-Fidelity Kit (Roche) was used for PCR, and the amplified DNA fragments were also cloned into the pET-26 (bp) vector between the compatible restriction sites. Site-directed mutagenesis was conducted using the Quik-Change mutagenesis kit (Stratagene) following the manufacturer's instructions. The sequences of the primers for mutagenesis are as follows: D217A mutation, 5'CTGACCCATCCGGAT-GCGCCGGTGAGCCGTCTG-3' (forward primer) and 5'-AGACGGCTCACCGGCGCATCCGGATGGGTCAG-3' (reverse primer).

Protein Expression and Purification. The plasmids harboring the genes were transformed into *E. coli* strain BL21 (DE3) (Novagen). The cells were grown in Luria-Bertani (LB) medium at 37° C. with vigorous shaking (220 rpm) until the OD600 reached 0.6-0.8. Isopropyl β-D-thiogalactopyranoside (IPTG, 0.5 mM) was added to induce protein expression, and the culture was grown for an additional 16 h at 16° C. Cells were harvested by centrifugation for 10 min at 5000 rpm. The cell pellet was frozen and thawed before the cells were lysed by sonication in 40 mL of lysis buffer [50 mM NaPi (pH 7.0)], 300 mMNaCl (200 mM for AxDGC2306-574), 5 mM mercaptoethanol (β-ME), 20 mM imidazole, 0.01% Triton X-100, and 0.2 mM phenylmethanesulfonyl fluoride (PMSF). The cell extract was centrifuged at 18000 rpm for 30 min. All the purification steps described below were performed at 4° C. The supernatant was filtered and loaded onto 1 mL of Ni2þ -NTA resin (GE Healthcare) that had been prepacked into a column. The flow-through was collected and passed through the column again. The column was washed with 50 mL of washing buffer (lysis buffer supplemented with 50 mM imidazole). The proteins were eluted by using the elution buffer (lysis buffer supplemented with 300 mM imidazole). After sodium dodecyl sulfate-polyacrylamide gel electrophoresis (SDS-PAGE) gel analysis, fractions with a purity of >95% were pooled together and desalted by using either a PD-10 desalting column (GE Healthcare) or a Superdex 200 gel filtration column (GE Healthcare) with the AKTAFPLC system. The molecular weight of the proteins was estimated on the basis of the standard curve generated with the standards. The bright-yellow looking proteins were concentrated using an Amicon concentrator (Millipore) and were stored at −80° C. after the measurement of protein concentration by a Bradford assay. The typical protein yield for wild-type and mutant AxDGC2 is 1-2 mg/L of culture. The final storage buffer was comprised of 50 mM Tris-HCl (pH 8.0), 50 mM NaCl, 5% glycerol, and 1 mM dithiothreitol (DTT).

For HPLC analysis, AxDGC2 was denatured with 1% TFA and the protein precipitate was removed by centrifugation. The yellow supernatant was loaded onto the Agilent LC1200 HPLC system column equipped with an XDBC18 column (4.6 mm_150 mm). The mobile phase is a gradient from 100% $H_2O$ to 100% acetonitrile (with 0.045% TFA) over 100 min with a flow rate of 1 mL/min; 100 μM standards (Sigma) were also applied to the column using the same mobile phase. c-di-GMP bound by AxDGC2 and its truncated construct were analysed.

Figure 6:
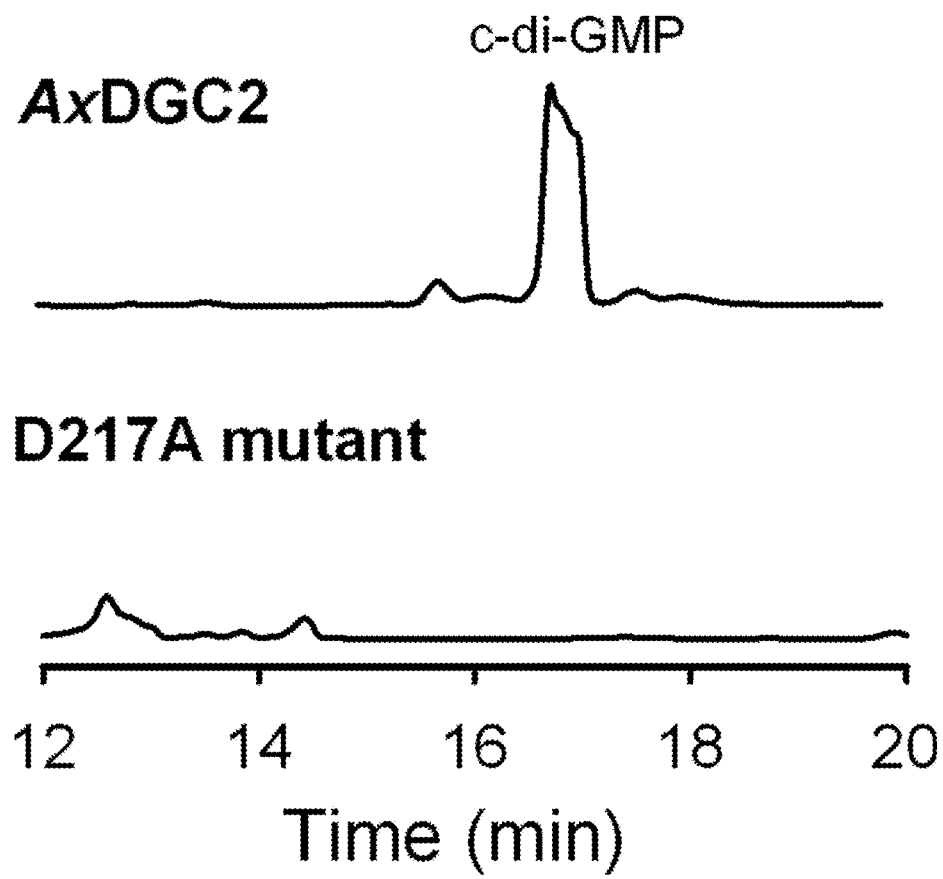
FIG. 6. Comparison of HPLC analysis of the binding of c-di-GMP by the GGDEF domain at the I-site between a wild type AxDGC2 and a D217A mutation.

HPLC analysis of the extract from the denatured protein solution revealed a small ligand bound by the protein. The small ligand was identified to be c-di-GMP by comparison with the standard using HPLC (FIG. 6A). C-di-GMP is most likely to be bound by the GGDEF domain at the inhibitory site (1-site). Sequence alignment showed the key residues, for c-di-GMP binding in the I-site. To test whether c-di-GMP is indeed bound at the I-site, we mutated a conserved residue (Asp217) in the putative I-site. HPLC analysis of the denatuted protein solution of mutant D217A showed that the protein was no longer associated with c-di-GMP (FIG. 6B) as c-di-GTP was unable to bind at the mutated I-site of the AxDGC2 mutant D217A.

Figure 7:
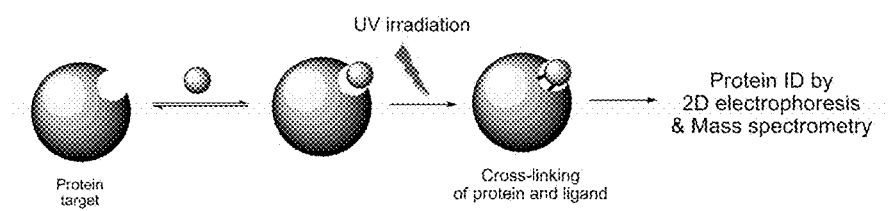
FIG. 7. Photo cross-linking strategy for identifying cyclic-di-GMP receptors. The small ball represents the functional cyclic-di-GMP.\

Production of Radioactive $^{32}$P-Cyclic-di-GMPand Other Analogues Using the tDGC Enzyme We have also demonstrated that the tDGC enzyme can be used to produce functional cyclic-di-GMP derivatives with potential applications in research labs. One of the most important goals in the cyclic-di-GMP signaling field is to identify the protein receptors or targets that bind cyclic-di-GMP. The most powerful method of identifying protein targets is through the use of photo-cross-linking ligands (FIG. 7). Thus, the development of functional cyclic-di-GMP that can be conjugated to the protein target is highly desirable.

Figure 8:
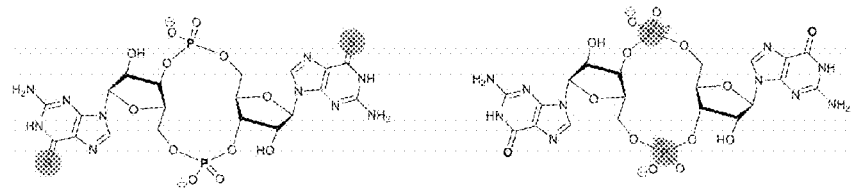
FIG. 8. 6-Thio cyclic-di-GMP and $^{32}P$ cyclic-di-GMP synthesized by the tDGC enzyme.

The structures of the two synthesized cyclic-di-GMP derivatives are shown in Table. 2 and FIG. 8. The 6-thio cyclic-di-GMP (structure on the left) is designed to be used as a photo cross-linking agent by taking advantaging of the unique photochemistry of the thio-guanine moiety. The molecule will be a useful in identifying the cellular proteins that directly binds to cyclic-di-GMP. The 32P-radioisotope-labelled cyclic-di-GMP on the right will be useful in validating the protein receptors for cyclic-di-GMP as well as detecting cyclic-di-GMP hydrolyzing enzymes.

TABLE 2 analogues manufactured enzymatically with the tDGC enzyme

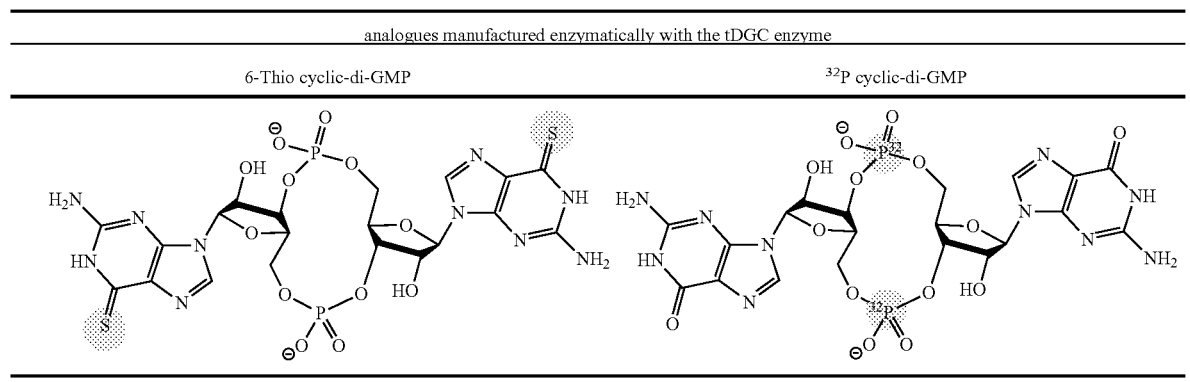

6-Thio cyclic-di-GMP                $^{32}$P cyclic-di-GMP

Figure 9:
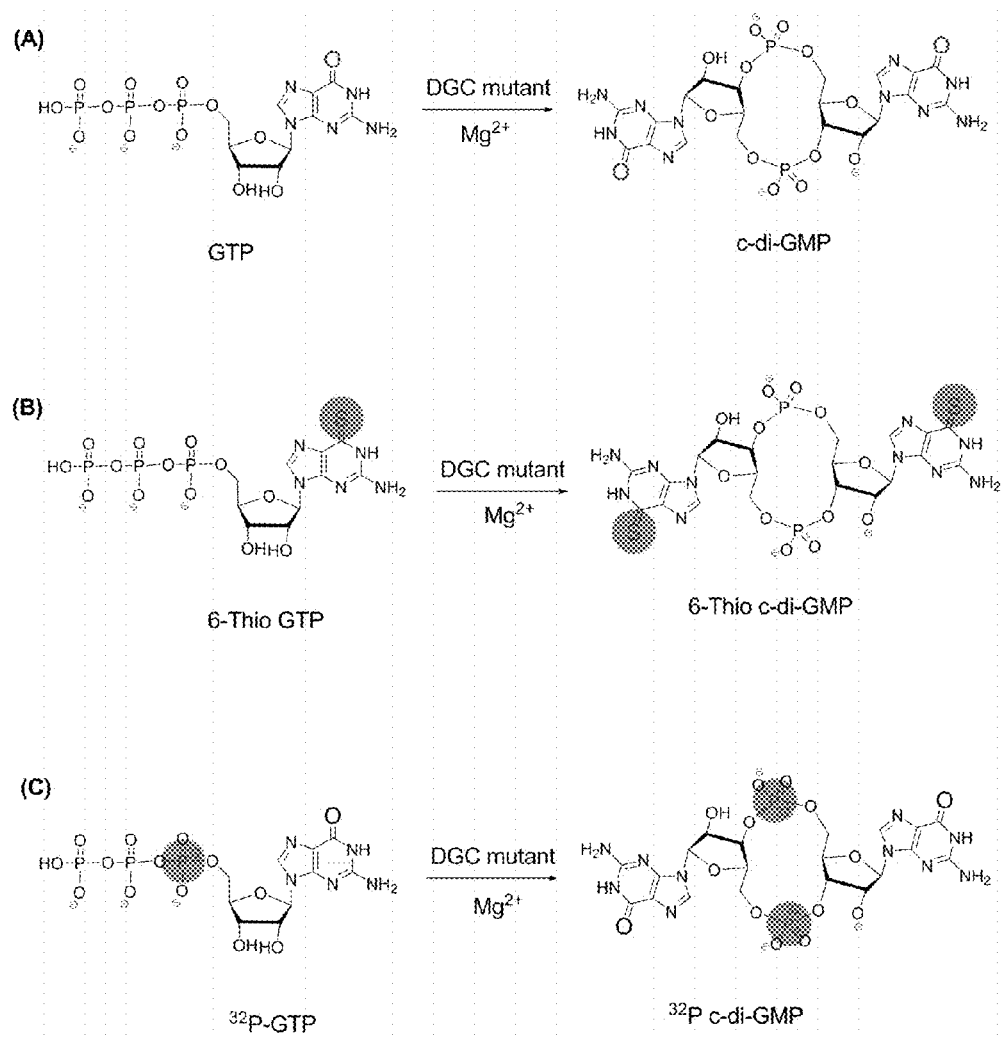
FIG. 9. A depiction of the enzymatic production using a mutant diguanylate cyclase of (A) cylic-di-GMP; (B) 6-Thio cyclic-di-GMP; and (C) $^{32}P$ cyclic-di-GMP.

The enzymatic production of cyclic-di GMP is depicted in FIG. 9. The 6-thio c-di-GMP was made by using 6-Thio GTP as a substrate (FIG. 9B), whereas the $^{32}$P c-di-GMP were made by using $^{32}$P-labelled GTP as the substrate for tDGC enzymatic conversion to $^{32}$P c-di-GMP (FIG. 9C). 6-Thio c-di-GMP has never been reported before. Previous attempts to make $^{32}$P labeled c-di-GMP using WspR or PleD has resulted in most of the $^{32}$P-labelled GTP being wasted due to low turnover. tDGC is a much effective enzyme for this task because it turns over essentially all the $^{32}$P-labelled GTP.

Immobilization of tDGC in Sol-Gel Matrix for Enzyme Preservation and Continuous Production The current production of cyclic-di-GMP by using tDGC still requires the separation of the enzyme and product at the end of the enzymatic reaction. Immobilization of the enzyme would allow the continuous production of cyclic-di-GMP without denaturing and separating the enzyme. For this purpose, we have trapped the tDGC enzyme in the Sol-Gel matrix by using a mild condition that prevents the enzyme from denaturation during immobilization. We have prepared the Sol-Gel beads with tDGC trapped inside. The enzyme inside the beads is active in synthesizing cyclic-di-GMP and highly stable with a shelf lifetime of months. The entrapment of tDGC enzyme in Sol-Gel has proven to be a useful method for improving the efficiency of cyclic-di-GMP synthesis and reducing production cost.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g., size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with reference to specific methods and embodiments, it will be appreciated that various modifications and changes may be made without departing from the invention.

We claim:

1. A diguanylate cyclase polypeptide according to a sequence selected from the group consisting of SEQ ID NO.: 2, SEQ ID NO.: 3, and SEQ ID NO.: 4.

2. The diguanylate cyclase polypeptide of claim 1 wherein the diguanylate cyclase comprises a monomer in solution.

3. The diguanylate cyclase polypeptide of claim 1 wherein the diguanylate cyclase is coupled to a support.

4. The diguanylate cyclase polypeptide of claim 3 wherein the support is a sol-gel.

5. The diguanylate cyclase polypeptide of claim 1 wherein the diguanylate cyclase polypeptide is synthesized chemically.

6. A method of manufacturing cyclic-di-GMP or cyclic-di-GMP analogues comprising the steps of:

incubating the diguanylate cyclase polypeptide of claim 1 with Guanosine-5'-triphosphate; and isolating the cyclic-di-GMP or cyclic-di-GMP analogues.

7. The method of claim 6 wherein the analogue comprises 6-thio cyclic-di GMP.

8. The method of claim 6 wherein the analogue comprises 32P-radioisotope-labelled cyclic-di-GMP.

* * * * *